(12) United States Patent
Farrell

(10) Patent No.: US 12,303,620 B2
(45) Date of Patent: May 20, 2025

(54) HYDROPHILIC COATINGS FOR MEDICAL DEVICES

(71) Applicant: HOLLISTER INCORPORATED, Libertyville, IL (US)

(72) Inventor: David J. Farrell, Ballina (IE)

(73) Assignee: Hollister Incorporated, Libertyville, IL (US)

( * ) Notice: Subject to any disclaimer, the term of this patent is extended or adjusted under 35 U.S.C. 154(b) by 886 days.

(21) Appl. No.: 17/287,804

(22) PCT Filed: Oct. 11, 2019

(86) PCT No.: PCT/US2019/055822
§ 371 (c)(1),
(2) Date: Apr. 22, 2021

(87) PCT Pub. No.: WO2020/086302
PCT Pub. Date: Apr. 30, 2020

(65) Prior Publication Data
US 2021/0316045 A1    Oct. 14, 2021

Related U.S. Application Data

(60) Provisional application No. 62/750,314, filed on Oct. 25, 2018.

(51) Int. Cl.
| A61L 29/08 | (2006.01) |
| A61L 29/00 | (2006.01) |
| A61L 29/04 | (2006.01) |
| A61L 29/16 | (2006.01) |
| C08L 39/06 | (2006.01) |

(52) U.S. Cl.
CPC ............ *A61L 29/085* (2013.01); *A61L 29/005* (2013.01); *A61L 29/041* (2013.01); *A61L 29/16* (2013.01); *C08L 39/06* (2013.01); *A61L 2300/428* (2013.01); *A61L 2400/10* (2013.01)

(58) Field of Classification Search
CPC ..... A61L 29/085; A61L 29/16; A61L 2400/10
See application file for complete search history.

(56) References Cited

U.S. PATENT DOCUMENTS

| 5,714,360 | A | 2/1998 | Swan et al. | |
| 6,110,483 | A * | 8/2000 | Whitbourne | ............ A61L 29/16 424/94.64 |
| 6,458,867 | B1 * | 10/2002 | Wang | ...................... A61F 2/966 523/105 |
| 6,610,035 | B2 | 8/2003 | Yang et al. | |
| 6,825,273 | B2 | 11/2004 | Duan et al. | |
| 7,402,620 | B2 | 7/2008 | McGhee | |

(Continued)

FOREIGN PATENT DOCUMENTS

| CA | 3052222 A1 | 8/2018 |
| WO | 0123015 A1 | 4/2001 |

OTHER PUBLICATIONS

International Search Report and Written Opinion for International Application No. PCT/US2019/055822, dated Jan. 24, 2020.

(Continued)

*Primary Examiner* — Robert A Vetere
(74) *Attorney, Agent, or Firm* — Cook Alex Ltd.

(57) ABSTRACT

Lubricious hydrophilic coatings and methods of making the same.

8 Claims, 1 Drawing Sheet

(56) References Cited

U.S. PATENT DOCUMENTS

| | | |
|---|---|---|
| 7,691,476 B2 | 4/2010 | Finley |
| 8,287,890 B2 | 10/2012 | Elton |
| 8,312,836 B2 | 11/2012 | Corbeil et al. |
| 8,329,157 B2 | 12/2012 | Hossainy et al. |
| 9,012,506 B2 | 4/2015 | Faucher et al. |
| 2006/0083768 A1 | 4/2006 | Labrecque et al. |
| 2010/0004738 A1 | 1/2010 | Herweck et al. |
| 2010/0209473 A1 | 8/2010 | Dhont et al. |
| 2012/0016038 A1 | 1/2012 | Faucher et al. |
| 2013/0261566 A1 | 10/2013 | Lockwood et al. |
| 2014/0178447 A1* | 6/2014 | Modak .................. A61K 36/28 424/407 |
| 2016/0263285 A1 | 9/2016 | Rostami et al. |
| 2017/0028105 A1 | 2/2017 | Ahlering et al. |

OTHER PUBLICATIONS

European Office Action for European Application No. 19797455.3 Dated Jan. 31, 2023.

* cited by examiner

HYDROPHILIC COATINGS FOR MEDICAL DEVICES

The present application is the U.S. National Stage Application of PCT Application No. PCT/US2019/055822, filed Oct. 11, 2019, which claims the priority of and benefit to U.S. Provisional Patent Application Ser. No. 62/750,314, filed Oct. 25, 2018, both of which are hereby incorporated herein by reference.

TECHNICAL FIELD

The present disclosure generally relates to hydrophilic coatings including a non-ionic liquid and methods of making the same. Furthermore, the present disclosure relates to medical devices having such hydrophilic coatings applied thereto and a method for making medical devices having such hydrophilic coatings thereon.

BACKGROUND

It is desirable for medical devices that are inserted into the body to have a lubricated or lubricious outer surface to facilitate insertion into and/or removal from the body. Such devices may include, for example, urinary catheters, endoscopes, cardiovascular catheters, syringes, vascular stents, etc. Such medical devices may have a lubricant gel placed on the outer surface of the device or may have a hydrophilic coating or layer disposed on the outer surface of the device. Hydrophilic coatings are becoming the preferred method of providing a lubricious surface because of their high lubricity and ease of use. Hydrophilic coatings become slippery or lubricious when lubricated with a liquid, such as saline or water. The lubricious hydrophilic coating eases insertion and removal of the device, minimizes soft tissue damage and reduces overall discomfort during use of the medical device.

When a medical device having a hydrophilic coating is used, the hydrophilic coating is typically hydrated for a certain period of time prior to use to activate the hydrophilic coating. For example, the user may immerse or otherwise contact the hydrophilic coating with a liquid, such as water, to hydrate or activate the coating. In some instances, the medical device is packaged in a packaging that includes liquid or water vapor within the package that hydrates the coating while the device is in the package so that the device is ready to use right out of the package.

SUMMARY

There are several aspects of the present subject matter which may be embodied separately or together in the devices and systems described and claimed below. These aspects may be employed alone or in combination with other aspects of the subject matter described herein, and the description of these aspects together is not intended to preclude the use of these aspects separately or the claiming of such aspects separately or in different combinations as set forth in the claims appended hereto.

In one aspect of the present disclosure, a lubricious hydrophilic coating with a hydration indicator. The hydrophilic coating becoming lubricious when hydrated with an amount hydration fluid and the hydrophilic coating having a first visual appearance when in a non-hydrated state and transitioning to a second visual appearance when in a hydrated state.

In another aspect, a medical device includes a hydrophilic coating disposed on a surface of the medical device, wherein the hydrophilic coating includes a non-polar liquid in an amount between 0.35 weight percent and about 80 weight percent of the coating.

In yet another aspect, a method of making a medical device having a hydrophilic coating. The method includes applying a solution of a non-polar liquid and an alcohol to a hydrophilic coating wherein the hydrophilic coating is disposed on the surface of a medical device. The non-polar liquid is about 0.01 weight percent to about 20 weight percent of the solution.

DETAILED DESCRIPTION

The present disclosure relates to lubricious hydrophilic coatings and devices having such coatings thereon. The hydrophilic coatings may be disposed on the surfaces of medical devices. Such medical devices may include shafts or tubes that may be inserted into and advanced within a lumen of a body, such as a urethra, esophagus, or fallopian tube. Such medical devices include urinary catheters, endovascular catheters, endoscopes, exploratory and biopsy devices, etc. While some of the embodiments set forth below may be described in the context of urinary catheters, the disclosure is not limited to such and the features disclosed herein may be applicable to any medical tubing that is inserted into a body lumen.

The hydrophilic coating on the surface of the medical device, such as a urinary catheter, may be any suitable hydrophilic coatings. For example, the hydrophilic coating may be formed from any suitable hydrophilic polymer. Such hydrophilic polymers may include but are not limited to polyvinylpyrrolidone (PVP), polyethylene oxide, polyurethanes, hyaluronic acid, homo- and copolymers of acrylic and methacrylic acid, polyvinyl alcohol, polyvinyl ethers, maleic anhydride based copolymers, polyesters, vinyl amines, polyethylenimines, poly(carboxylic acids), polyamides, polyanhydrides, polyphosphazenes, cellulosics, for example methyl cellulose, carboxymethyl cellulose, hydroxymethyl cellulose, and hydroxypropyl cellulose, other polysaccharides.

The hydrophilic coating may also include or be infused with a non-polar liquid, such as a hydrophobic liquid. The non-polar liquid may be an oil or oil-like substance. The oil or oil-like substance may be synthesized oil, a plant or a vegetable oil, or it may be derived from a plant or a vegetable oil. In one embodiment, the non-polar liquid is a tocopherol. The non-polar liquid also may be an essential oil, including but not limited to menthol, carvacrol, thymol, etc. and mixtures thereof, or a mixture of an essential oil with tocopherol. The non-polar liquid may provide any number of characteristics to the hydrophilic coating including but not limited to inducing chromism, antimicrobial effects, fragrances, providing lubricity (including providing supplemental and/or enhanced lubricity), and/or increasing dry-out times. The amount of non-polar liquid incorporated into the hydrophilic coating may vary depending on the application. For example, if a non-polar liquid, such as an essential oil, is incorporated into the coating to provide a pleasant fragrance, the non-polar liquid may be in an amount that is greater than about 0.35 weight percent of the coating. In other embodiments wherein the non-polar liquid provides other characteristics, the amount of non-polar liquid may be greater than about 3.5 weight percent or greater than about 5.0 weight percent. The non-polar liquid may be between about 3.5 weight percent and about 80 weight percent of the hydrophilic coating.

Figure 2:
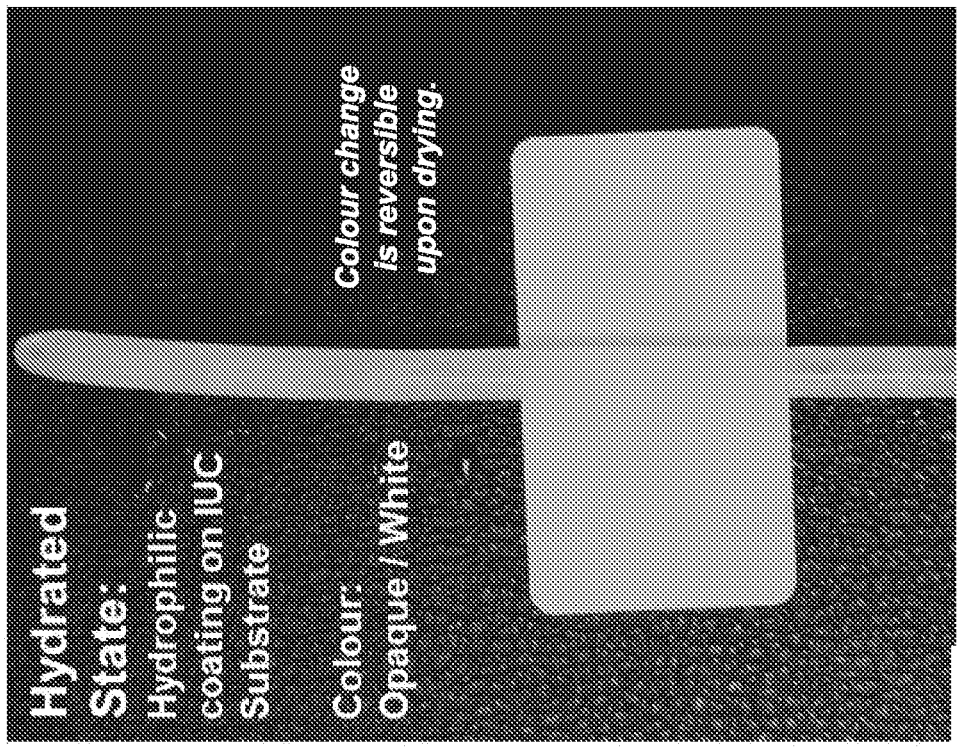
FIG. 2 is a picture of the hydrophilic catheter of FIG. 1 shown with the hydrophilic coating in a hydrated state and wherein the visual appearance of the coating has become more opaque or translucent as compared to the coatings visual appearance in FIG. 1.
Figure 1:
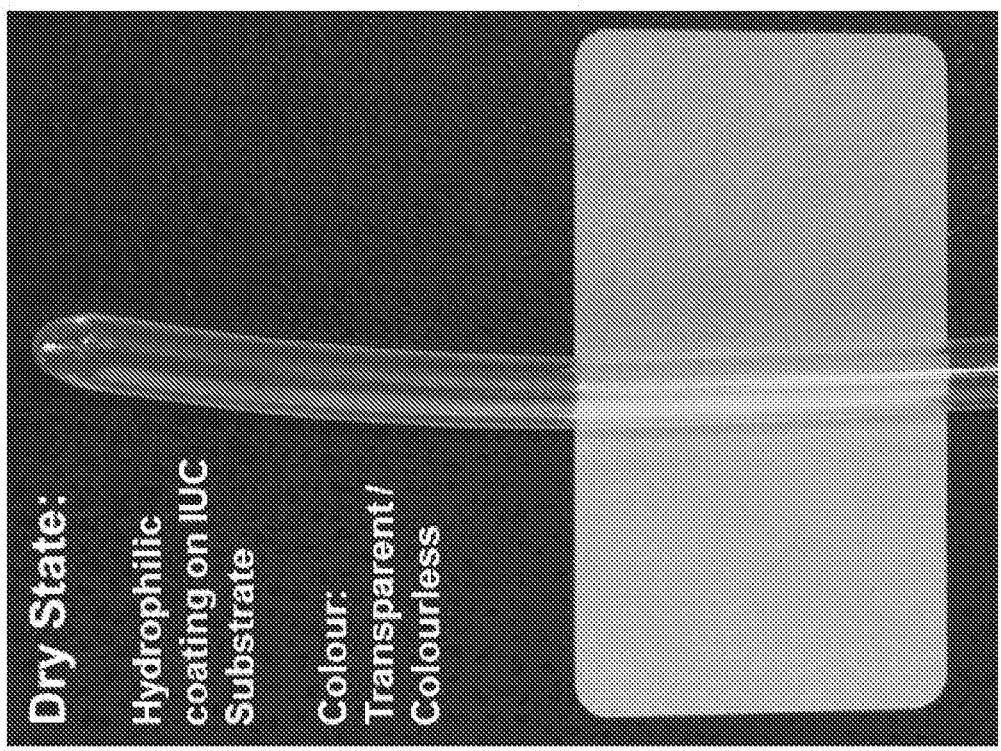
FIG. 1 is a picture of a hydrophilic catheter that includes a hydrophilic coating in a dry state, the hydrophilic coating will change in visual appearance when hydrated.

In one embodiment, the non-polar liquid may induce chromism wherein the hydrophilic coating changes in visual appearance depending on its environment. For example, the non-polar liquid may produce hydrochromic, thermochromic, photochromic, and/or solvatochromic responses. In one embodiment, the hydrophilic coating having a non-polar liquid may be hydrochromic in that the coating will change in visual appearance in response to being hydrated. In one embodiment, the hydrophilic coating may be transparent in the dry state and may be opaque or translucent in a hydrated state. For example, a hydrophilic coating may include between 3.5 weight percent and 80 weight percent of a non-polar liquid, such as a tocopherol, which may be alpha-tocopherol. As shown in FIG. 1, the dry hydrophilic coating of the catheter may have a transparent or colorless visual appearance. As shown in FIG. 2, when hydrated, the visual appearance of the hydrophilic coating changes to a more opaque or white appearance. Furthermore, the level of opaqueness may depend on the hydration amount of the hydrophilic coating and the change in appearance may take place gradually. Also, the change of the visual appearance may be reversible in that the visual appearance of the hydrophilic coating may change back upon drying.

One of the issues of incorporating a non-polar liquid into a hydrophilic material or coating is that the non-polar substances and hydrophilic material of the coating, in general, do not mix well. Because the substances do not mix well, it has been difficult to incorporate non-polar substances into hydrophilic coatings. When the hydrophilic coating formulations include water, it can be very difficult to incorporate an effective amount of oil into the coating. The hydrophilic coatings of the present disclosure include about 0.35 weight percent to about 80 weight percent non-polar liquid of the hydrophilic coating. In another embodiment, the non-polar liquid may be in an amount greater than about 3.5 weight percent or greater than about 5.0 weight percent. In one embodiment, a urinary catheter having a hydrophilic coating may include between about 0.02 grams and 0.15 grams of a non-polar liquid, such as a tocopherol.

One embodiment of making a medical device having a hydrophilic coating includes infusing a non-polar liquid into the coating. The method may include applying a solution of a non-polar liquid and an alcohol to the hydrophilic coating of the medical device. The non-polar liquid of the solution may be in amount between about 1 weight percent to about 20 weight percent of the solution. For example, the non-polar liquid may be in an amount of about 5 weight percent, 10 weight percent or 20 weight percent. The solution may be applied to the hydrophilic coating by dipping (immersion), spraying, bushing or any other means. The application or infusion period may be any suitable period. For example, when applied by dipping, the application or infusion period may be seconds or tens of seconds. After the solution is applied and infused into the coating, the alcohol is then evaporated or dried off from the coating, and optionally, the hydrophilic coating may be washed. The drying may take place under ambient conditions or may take place in an oven.

In one embodiment, a urinary catheter having a hydrophilic coating is dipped (immersed) into a solution of tocopherol and ethanol. The tocopherol may be alpha-tocopherol, and the tocopherol may be in an amount of between about 0.1 weight percent and about 20 weight percent of the solution. After the solution has been infused into the coating, the ethanol is then dried off from the hydrophilic coating and, optionally, the hydrophilic coating may be washed with water. The resulting hydrophilic catheter may include a hydrophilic coating that includes about 0.35 weight percent to about 80 weight percent of the infused non-polar liquid. In one embodiment, the hydrophilic coating may include between about 0.02 grams and 0.15 grams of a non-polar liquid, such as a tocopherol.

EXAMPLES

Example I

Samples of hydrophilically coated intermittent urinary catheters (sized 14 CH) were immersed in a 100% ethanol or alpha-tocopherol/ethanol solutions of varying concentrations of alpha tocopherol. The hydrophilic coatings of the catheters were formed from polyvinylpyrrolidone. Each of the samples was immersed in one of the solutions for a period of 10 to 60 seconds. The coating infused with the solution was washed by quickly dipping the catheter into a vessel containing pure ethanol to remove traces of infused alpha-tocopherol that may reside on the coatings surface. The treated catheters were then placed on mandrels to dry under gentle airflow at ambient temperature to remove the ethanol.

After ethanol removal, the catheters were immersed in water for four minutes to hydrate the hydrophilic coating. Initial coefficient of friction (CoF), abraded CoF and ten minute dry-out CoF were measured for each of the samples. The CoFs were measured using a Harland Friction Tester Model FTS6000. During the CoF measurement, the proximal end portion of the catheter is cut (40 mm from the tip end of the catheter) and a mandrel was inserted into the remaining section of the coated catheter tube. The tube was then clamped between two pieces of silicone rubber at 100 g applied load wherein the silicone rubber had a Shore hardness of 60 A. The clamp force being 200 g (two times the 100 g applied load). The tube with the mandrel inserted therein was pulled through the two pieces of silicone rubber at a speed of 10 mm/s. The force required to pull about 80 mm of the tube through the two pieces of silicone rubber was measured and recorded using a universal tensile tester equipped with a 200 N load cell. The CoF value was calculated from the ratio of recorded to applied loads (i.e., the recorded load divided by 2 times the applied load or 200 g) when steady state was reached.

$$CoF = \frac{\text{Average State Stage Force Recorded load}}{\text{Clamp Force}}$$

The initial CoF was measured immediately after the hydrophilic coating was hydrated. For the abraded CoF measurements, the hydrated catheters were placed in a water bath and abraded 50 times by passing the catheter tubes back and forth 25 times through 4.14 mm diameter hole in a 1 mm thick silicone pad with Shore hardness of 60 A. The abrading took place while the catheter was immersed in the water bath. This test is designed to remove any portions of the coating that are not well adhered to the catheter. After abrading, the CoF of the abraded catheters were measured in the above-described manner.

The CoF was also measured after a time minute dry out. For the dry-out CoF measurement, after the hydrophilic coating of the catheter was hydrated, it was placed in a controlled atmosphere with a constant relative humidity of 50% RH and a constant temperature of 23° C. for 10 minutes prior to measuring the CoF.

The CoF of the samples are listed below in Table 1.

TABLE 1

| Concentration (% w/v) A-Tocopherol in Ethanol | CoF Initial | CoF Abraded | CoF 10 min Dry Out |
|---|---|---|---|
| 0 | 0.013 | 0.009 | 0.016 |
| 0 | 0.013 | 0.012 | 0.018 |
| 0 | 0.013 | 0.008 | 0.016 |
| 0 | 0.014 | 0.009 | 0.019 |
| 0 | 0.013 | 0.008 | 0.014 |
| 0 | 0.010 | 0.008 | 0.017 |
| 1 | 0.013 | 0.008 | 0.019 |
| 1 | 0.013 | 0.011 | 0.017 |
| 1 | 0.014 | 0.007 | 0.022 |
| 1 | 0.017 | 0.011 | 0.018 |
| 1 | 0.017 | 0.008 | 0.021 |
| 1 | 0.016 | 0.010 | 0.022 |
| 5 | 0.025 | 0.014 | 0.024 |
| 5 | 0.022 | 0.013 | 0.031 |
| 5 | 0.017 | 0.011 | 0.025 |
| 5 | 0.043 | 0.012 | 0.059 |
| 5 | 0.018 | 0.010 | 0.024 |
| 5 | 0.018 | 0.011 | 0.024 |

The mean for CoF for the above samples is listed in Table 2.

TABLE 2

| Concentration (% w/v) A-Tocopherol in Ethanol | Mean CoF Initial | Mean CoF Abraded | Mean CoF 10 min Dry Out |
|---|---|---|---|
| 0% | 0.012 | 0.009 | 0.017 |
| 1% | 0.015 | 0.009 | 0.020 |
| 5% | 0.024 | 0.012 | 0.031 |

Example II

In this Example, samples of hydrophilically coated intermittent urinary catheters (sized 14 CH/40 cm) were immersed in a 100% ethanol or alpha-tocopherol/ethanol solutions of varying concentrations of alpha-tocopherol. The hydrophilic coatings of the catheters were formed from polyvinylpyrrolidone. Each of the samples was immersed in one of the solutions for a period of 60 seconds. The treated catheters were then placed on mandrels to dry under gentle airflow at ambient temperature to remove the ethanol. After ethanol removal, the weight of each catheter was then measured and recorded. The catheter was then immersed in water for four minutes to hydrate the hydrophilic coating. The catheter was then weighed and the difference in weight between the dry catheter and hydrated catheter was calculated to determine the amount of water retained in the hydrated catheter. Table 3 shows the results.

TABLE 3

| Concentration (% w/v) A-Tocopherol in Ethanol | Weight (g) Hydrated Catheter | Weight (g) Dried Catheter | Water Capacity (g) |
|---|---|---|---|
| 0 | 3.90 | 3.33 | 0.58 |
| 0 | 3.95 | 3.37 | 0.59 |
| 0 | 3.92 | 3.36 | 0.56 |
| 0 | 4.02 | 3.35 | 0.67 |
| 0 | 3.92 | 3.35 | 0.57 |
| 0 | 3.94 | 3.31 | 0.63 |
| 1 | 3.88 | 3.39 | 0.50 |
| 1 | 4.00 | 3.42 | 0.58 |
| 1 | 4.02 | 3.43 | 0.60 |
| 1 | 3.93 | 3.37 | 0.55 |
| 1 | 3.97 | 3.35 | 0.62 |
| 1 | 4.03 | 3.41 | 0.62 |
| 5 | 3.81 | 3.36 | 0.45 |
| 5 | 3.80 | 3.38 | 0.42 |
| 5 | 3.77 | 3.34 | 0.43 |
| 5 | 3.80 | 3.36 | 0.44 |
| 5 | 3.85 | 3.35 | 0.50 |
| 5 | 3.76 | 3.38 | 0.38 |

The mean amount of water retained for the above samples is listed in Table 4.

TABLE 4

| Concentration (% w/v) A-Tocopherol in Ethanol | Mean Water Capacity (g) |
|---|---|
| 0% A-T | 0.60 |
| 1% A-T | 0.58 |
| 5% A-T | 0.43 |

Example III

In this Example, samples of hydrophilically coated intermittent urinary catheters (sized 14 CH/40 cm) were weighed and the weight was recorded. The hydrophilic coatings of the catheters were formed from polyvinylpyrrolidone. The hydrophilic coatings of the catheters were immersed for one minute in alpha-tocopherol/ethanol solutions of varying concentrations of alpha-tocopherol. The thus treated catheters were then placed on mandrels to dry under gentle airflow at ambient temperature to remove the ethanol. After ethanol removal, the weight of each catheter was then measured and the difference in weight between the catheter prior to immersion in the solution and after the immersion and drying was calculated to determine the amount of alpha-tocopherol retained in the catheter. The results are shown in Tables 5-8 below.

TABLE 5

| Sample # | W1 Before Dipping (g) | W2 After Dipping (g) | Solution concentration % w/w in Ethanol | Difference Amount (g) |
|---|---|---|---|---|
| 1 | 5.6756 | 5.7096 | 1% | 0.0340 |
| 2 | 5.6548 | 5.687 | 1% | 0.0322 |
| 3 | 5.6728 | 5.7053 | 1% | 0.0325 |
| 4 | 5.6483 | 5.6688 | 1% | 0.0205 |
| 5 | 5.6730 | 5.7052 | 1% | 0.0322 |
| 6 | 5.6755 | 5.7083 | 1% | 0.0328 |
| 7 | 5.6584 | 5.7029 | 1% | 0.0445 |
| 8 | 5.6578 | 5.6938 | 1% | 0.0360 |

TABLE 5-continued

| Sample # | W1 Before Dipping (g) | W2 After Dipping (g) | Solution concentration % w/w in Ethanol | Difference Amount (g) |
|---|---|---|---|---|
| 9 | 5.6593 | 5.6946 | 1% | 0.0353 |
| 10 | 5.6977 | 5.7291 | 1% | 0.0314 |
| 11 | 5.6707 | 5.7026 | 1% | 0.0319 |
| 12 | 5.6630 | 5.7037 | 1% | 0.0407 |
| Mean point | | | | 0.0337 |

TABLE 6

| Sample # | W1 Before Dipping (g) | W2 After Dipping (g) | Solution concentration % w/w in Ethanol | Difference Amount (g) |
|---|---|---|---|---|
| 1 | 5.6656 | 5.6976 | 5% | 0.0320 |
| 2 | 5.6335 | 5.689 | 5% | 0.0555 |
| 3 | 5.6216 | 5.6707 | 5% | 0.0491 |
| 4 | 5.6537 | 5.7152 | 5% | 0.0615 |
| 5 | 5.6023 | 5.6497 | 5% | 0.0474 |
| 6 | 5.6351 | 5.681 | 5% | 0.0459 |
| 7 | 5.6747 | 5.7223 | 5% | 0.0476 |
| 8 | 5.6543 | 5.7048 | 5% | 0.0505 |
| 9 | 5.6892 | 5.7416 | 5% | 0.0524 |
| 10 | 5.6503 | 5.7015 | 5% | 0.0512 |
| 11 | 5.6634 | 5.7148 | 5% | 0.0514 |
| Mean Difference | | | | 0.0495 |

TABLE 7

| Sample # | W1 Before Dipping (g) | W2 After Dipping (g) | Solution concentration % w/w in Ethanol | Difference Amount (g) |
|---|---|---|---|---|
| 1 | 5.6620 | 5.7146 | 10% | 0.0526 |
| 2 | 5.7117 | 5.7637 | 10% | 0.0520 |
| 3 | 5.6729 | 5.7388 | 10% | 0.0659 |
| 4 | 5.6891 | 5.7400 | 10% | 0.0509 |
| 5 | 5.7007 | 5.7683 | 10% | 0.0676 |
| 6 | 5.7418 | 5.7964 | 10% | 0.0546 |
| 7 | 5.7260 | 5.7936 | 10% | 0.0676 |
| 8 | 5.6821 | 5.7548 | 10% | 0.0727 |
| 9 | 5.6898 | 5.7652 | 10% | 0.0754 |
| 10 | 5.6496 | 5.7226 | 10% | 0.0730 |
| 11 | 5.7052 | 5.7916 | 10% | 0.0864 |
| 12 | 5.7464 | 5.8299 | 10% | 0.0835 |
| Mean Difference | | | | 0.0669 |

TABLE 8

| Sample # | W1 Before Dipping (g) | W2 After Dipping (g) | Solution concentration % w/w in Ethanol | Difference Amount (g) |
|---|---|---|---|---|
| 1 | 5.6930 | 5.8046 | 20% | 0.1116 |
| 2 | 5.7222 | 5.8332 | 20% | 0.1110 |
| 3 | 5.7087 | 5.8371 | 20% | 0.1284 |
| 4 | 5.7236 | 5.8473 | 20% | 0.1237 |
| 5 | 5.7486 | 5.8739 | 20% | 0.1253 |
| 6 | 5.7124 | 5.8486 | 20% | 0.1362 |
| 7 | 5.7061 | 5.8226 | 20% | 0.1165 |
| 8 | 5.7488 | 5.851 | 20% | 0.1022 |
| 9 | 5.6767 | 5.7965 | 20% | 0.1198 |
| 10 | 5.6784 | 5.8108 | 20% | 0.1324 |
| 11 | 5.7028 | 5.8447 | 20% | 0.1419 |
| 12 | 5.6763 | 5.8186 | 20% | 0.1423 |
| Mean Difference | | | | 0.1243 |

It will be understood that the embodiments described above are illustrative of some of the applications of the principles of the present subject matter. Numerous modifications may be made by those skilled in the art without departing from the spirit and scope of the claimed subject matter, including those combinations of features that are individually disclosed or claimed herein. For these reasons, the scope hereof is not limited to the above description but is as set forth in the following claims, and it is understood that claims may be directed to the features hereof, including as combinations of features that are individually disclosed or claimed herein.

What is claimed is:

1. A urinary catheter, comprising:
   a hydrophilic coating disposed on an outer surface of the urinary catheter wherein the hydrophilic coating includes tocopherol in an amount greater than 3.5 weight percent of the hydrophilic coating; and
   the hydrophilic coating having a first visual appearance when in a non-hydrated state and transitioning to a second visual appearance when in a hydrated state.

2. The urinary catheter of claim 1, wherein the transition from the first visual appearance to the second visual appearance is a gradual transition that depends on the amount of hydration fluid absorbed into the hydrophilic coating.

3. The urinary catheter of claim 1, wherein transparency of the hydrophilic coating varies between the first visual appearance and the second visual appearance.

4. The urinary catheter of claim 1, wherein the tocopherol is an amount of about 0.02 grams and 0.15 grams.

5. The urinary catheter of claim 1, wherein the first visual appearance is transparent and the second visual appearance is opaque or translucent.

6. The urinary catheter of claim 1, wherein a color of the hydrophilic coating varies between the first visual appearance and the second visual appearance.

7. The urinary catheter of claim 6, wherein the first visual appearance is a first color and the second visual appearance is a second color that is different from the first color.

8. The urinary catheter of claim 1, wherein the amount of tocopherol is between about 3.5 weight percent and about 80 weight percent of the hydrophilic coating.

* * * * *